United States Patent [19]
Petrakis et al.

[11] Patent Number: 4,853,476
[45] Date of Patent: Aug. 1, 1989

[54] PHOSPHORUS CONTAINING COMPOUNDS AS INHIBITORS OF ENKEPHALINASES

[75] Inventors: Konstaninos S. Petrakis, Montclair; Joel G. Berger, Verona; Elijah H. Gold, West Orange, all of N.J.

[73] Assignee: Schering Corporation, Kenilworth, N.J.

[21] Appl. No.: 102,753

[22] Filed: Sep. 24, 1987

Related U.S. Application Data

[63] Continuation of Ser. No. 685,511, Dec. 24, 1984, abandoned.

[51] Int. Cl.[4] .................................................. C07F 9/09
[52] U.S. Cl. ..................................... 558/170; 549/221
[58] Field of Search .......................... 558/170; 549/221

[56] References Cited

U.S. PATENT DOCUMENTS

| 4,316,896 | 2/1982 | Thorsett et al. | 558/170 |
| 4,423,242 | 12/1983 | Wilkinson et al. | 560/41 |
| 4,432,972 | 2/1984 | Karanewsky et al. | 558/171 |

FOREIGN PATENT DOCUMENTS

| 38046 | 10/1981 | European Pat. Off. . |
| 75334 | 3/1983 | European Pat. Off. . |
| 82088 | 6/1983 | European Pat. Off. . |

Primary Examiner—Anton H. Sutto
Attorney, Agent, or Firm—Henry P. Nowak; Richard C. Billups; James R. Nelson

[57] ABSTRACT

Novel phosphorous containing compounds and compositions containing said compounds inhibit the actions of enkephalinases in mammals. Methods for preparing said compounds and compositions and methods for their use to elicit analgesia and treat mental disorders are described.

Useful intermediates for preparing the compounds are also described.

9 Claims, No Drawings

PHOSPHORUS CONTAINING COMPOUNDS AS INHIBITORS OF ENKEPHALINASES

This is a continuation of application Ser. No. 685,511 filed Dec. 24, 1984, now abandoned.

BACKGROUND OF THE INVENTION

Enkephalin is a natural opiate receptor agonist and is believed to be a mixture of two pentapeptides: H—Tyr—Gly—Gly—Phe—Met—OH (methionine-enkephalin), and H—Tyr—Gly—Gly—Phe—Leu—OH (leucine-enkephalin). Hereinafter, the name enkephalin is used generically to embrace all such compounds.

It has been reported by Beluzzi et.al., Nature, 260, 625 (1976), that when enkephalin is injected into the brain ventricle of rats, a profound analgesia is obtained. It is also known in the art that enkephalin is acted upon by a group of enzymes known generically as enkephalinases, which are also naturally occurring and is inactivated thereby. The present invention provides a method for inhibiting the action of enkephalinases, and compounds useful for accomplishing said method.

The following European Patent Application Nos. 81102770.5, 82108858.0, and 82402314.7 (publication Nos. 38046, 75334, and 82088, respectively) disclose certain phosphorous containing compounds which are described as possessing enkephalinase-inhibiting activity.

SUMMARY OF THE INVENTION

The invention sought to be patented in its first chemical compound aspect is a compound having the structural formula I:

$$W-P(O)OR^1-V-CHR^3-C(O)-NH-Z-C(O)R^2 \qquad I$$

wherein $R^1$ is hydrogen, alkyl having from 1 to 6 carbon atoms, cycloalkyl having from 3 to 7 carbon atoms, alkylcycloalkyl having from 4 to 13 carbon atoms, $CR^{11}HOC(O)R^{12}$ [wherein $R^{11}$ is alkyl having from 1 to 6 carbon atoms or cycloalkyl having from 5 to 7 carbon atoms, $R^{12}$ is alkyl having from 1 to 6 carbon atoms or cycloalkyl having from 5 to 7 carbon atoms] or

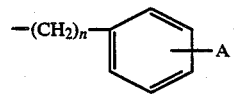

[wherein n is O or an integer of from 1–6, A is hydrogen, halogen, hydroxy, nitro, trifluoromethyl, alkoxy having from 1 to 6 carbon atoms, alkyl having from 1 to 6 carbon atoms, 2- or 3-thienyl or phenyl which may be substituted with halogen, hydroxy, nitro, trifluoromethyl, alkoxy having from 1 to 6 carbon atoms, or alkyl having from 1 to 6 carbon atoms];

W is $R^1$ or $OR^1$ wherein $R^1$ is defined herein provided that $R^1$ is not hydrogen directly bonded to phosphorus or $CR^{11}HOC(O)R^{12}$ wherein $R^{11}$ and $R^{12}$ are defined herein;

V is oxygen, sulfur or $NR^{13}$ [wherein $R^{13}$ is hydrogen, alkyl having from 1 to 6 carbon atoms or aralkyl];

$R^3$ is 2- or 3-thienylmethyl, 3-indolylmethyl, alkyl having from 1 to 6 carbon atoms, cycloalkyl having from 3 to 7 carbon atoms, cycloalkylmethyl having from 4 to 8 carbon atoms or

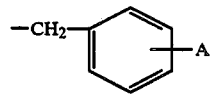

[wherein A is defined herein];

Z is o-, m- or p-phenylene, —$(CHR^4)_r$— [wherein r is 2, 3, or 4 and $R^4$ is independently chosen from hydrogen, alkyl having from 1 to 6 carbon atoms, cycloalkyl having from 3 to 7 carbon atoms, cycloalkylmethyl having from 4 to 8 carbon atoms, 3-indolylmethyl, hydroxymethyl, 2-(methylthio)ethyl,

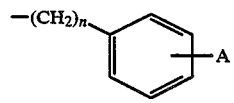

wherein n and A are defined herein), $R^{14}NC(O)OR^{15}$ or $R^{14}NC(O)R^{15}$ (wherein $R^{14}$ is hydrogen or alkyl having from 1 to 6 carbon atoms, $R^{15}$ is alkyl having from 1 to 6 carbon atoms or —$(CH_2)_n$ [wherein n and A are defined herein])]; and $R^2$ is hydroxy, alkoxy having from 1 to 6 carbon atoms,

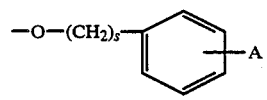

[wherein A is defined herein and s is 0, 1, 2 or 3],

—O—$(CR^5R^6)OCOR^7$ [wherein $R^5$ and $R^6$ may be the same or different and are hydrogen or alkyl having from 1 to 6 carbon atoms, $R^7$ is

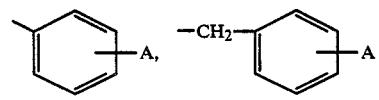

or alkyl having from 1 to 6 carbon atoms],

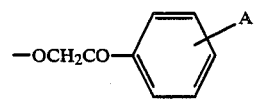

(wherein A is defined herein),

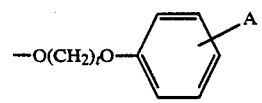

[wherein A is defined herein and t is 1 or 2],

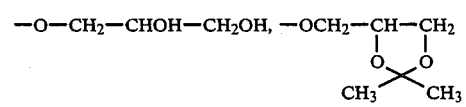

-continued

—O(CH$_2$)$_u$O— 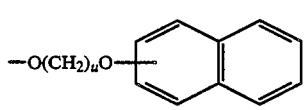 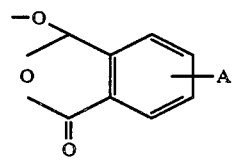

[wherein u is 1 or 2], [wherein A is defined herein] or NR$^8$R$^9$ [wherein R$^8$ is

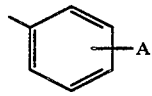

(wherein A is defined herein), R$^9$ is hydrogen or alkyl having from 1 to 6 carbon atoms].

Preferred values for the above-defined groups are as follows:

R$^1$ is hydrogen, methyl, ethyl, phenyl, benzyl, phenylethyl or —CR$^{11}$HOC(O)R$^{12}$ wherein R$^{11}$ and R$^{12}$ are defined herein;

R$^2$ is hydroxy, methoxy, ethoxy, propoxy, phenoxyethyloxy, pivaloyloxymethyloxy, —OCH$_2$CHOHCH$_2$OH or —OCH$_2$—CH—CH$_2$ ;
         |    |
         O    O
          \\  /
           C
          / \\
       CH$_3$  CH$_3$ W is hydroxy, alkyl having from 1 to 6 carbon or

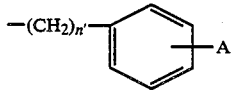

[wherein n' is an integer of from 1-6, A is hydrogen, fluorine or chlorine;

VC*HR$^3$ contains an asymmetric carbon (C*) the chirality of which is the S absolute configuration wherein V is oxygen and wherein R$^3$ is [

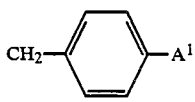

wherein (A$^1$ is hydrogen, phenyl, fluorine, chlorine or trifluoromethyl)]; and Z is p-phenylene, or —CH$_2$CHR$^4$—, wherein R$^4$ is hydrogen, hydroxy, methoxy, methyl or benzyl.

The most preferred values for the above-defined groups are as follows:

R$^1$ is hydrogen or —CHR$^{11}$OC(O)R$^{12}$ wherein R$^{11}$ and R$^{12}$ are defined herein;

R$^2$ is hydroxy, methoxy, ethoxy or propoxy;

W is hydroxy, alkyl having from 1 to 6 carbon atoms or

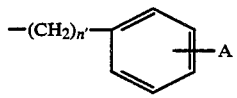

[wherein n' is an integer of from 1-6 and A is hydrogen, fluorine or chlorine];

VC*HR$^3$ contains an assymetric carbon (C*) the chirality of which is the S absolute configuration wherein V is oxygen and wherein R$^3$ is

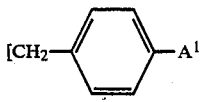

(wherein A$^1$ is hydrogen, fluorine, chlorine, phenyl or trifluoromethyl)]; and Z is p-phenylene or —CH$_2$CHR$^4$—, wherein R$^4$ is hydrogen, hydroxy, methoxy, methyl or benzyl.

The invention sought to be patented in its first pharmaceutical method aspect is a method for inhibiting the action of enkephalinases in a mammal to thereby elicit an analgesic effect in said mammal, which method comprises administering an enkephalinase inhibitory effective amount of a compound having structural formula I to said mammal.

The invention sought to be patented in its first pharmaceutical composition aspect is a composition useful for inhibiting the action of enkephalinases in a mammal, which composition comprises a compound having the structural formula I in combination with a pharmaceutically acceptable carrier.

The invention sought to be patented in its second pharmaceutical method aspect is a method for eliciting analgesia in a mammal which method comprises administering an analgesic effective amount of a compound having structural formula I to said mammal.

The invention sought to be patented in its second pharmaceutical composition aspect is a composition useful for eliciting analgesia in a mammal which composition comprises a compound having structural formula I in combination with a pharmaceutically acceptable carrier.

The invention sought to be patented in its third pharmaceutical method aspect is a method for treating mental disorders such as depression and schizophrenia in a patient which method comprises administering a clinically effective amount of a compound having structural formula I to said patient.

The invention sought to be patented in its third pharmaceutical composition aspect is a composition useful for treating mental disorders such as depression and schizophrenia in a patient which composition comprises a compound having structural formula I in combination with a pharmaceutically acceptable carrier.

DESCRIPTION OF THE INVENTION

The compounds of the invention having structural formula I may be prepared for example, by reacting a compound having structural formula II with a compound III producing a compound of structure IV.

EQUATION 1

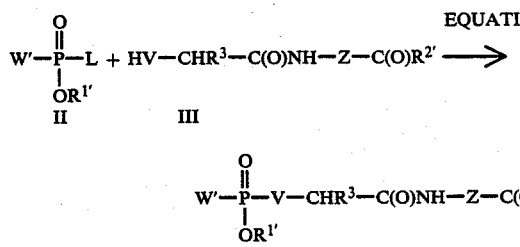

The phosphorylation reaction proceeds efficiently in inert organic solvents such as methylene chloride, toluene, or ethyl acetate in the presence of tertiary amine bases such as triethylamine, pyridine or dimethylaminopyridine at 0° C. or reflux temperatures.

In the above formulas W', $R^{1'}$ and $R^{2'}$ have the meaning as herein defined for W, $R^1$ and $R^2$ with the following restrictions: W' and $R^{2'}$ cannot be hydroxyl and $R^{1'}$ hydrogen. V, $R^3$ and Z are as herein defined. L is a leaving group such as halogen or an ester of sulfonic acid such as a p-toluenesulfonyloxy or trifluoromethylsulfonyloxy derivative.

Compounds II are readily available substances, either commercially available or synthesizable via standard phosphorous chemistry techniques (*Methoden Organischen Chemie, Houben-Weyl*, Vol. 12/1, 1963). Compounds of structure III are dipeptides which can be obtained readily via standard peptide bond forming reactions between a carboxylic acid V and an amine VI as shown in Equation 2. Such reactions have been reviewed in, for example, "The Peptides: Analysis, Synthesis, Biology", Vol. 1 (Major Methods of Peptide Bond Formation), E. Gross and J. Meienhoffer eds., Academic Press 1979.

EQUATION 2

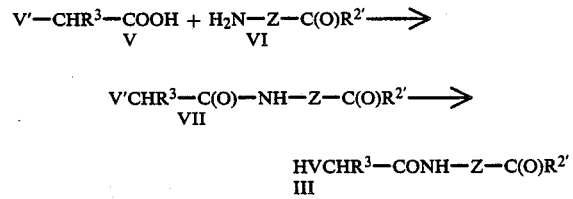

where V' is a suitably protected form of group HV such as $(CH_3)_3COC(O)V$ or $Ar-CH_2OC(O)V$. Compounds of structure V can be synthesized using standard amino acid chemistry procedures. When HV is OH or SH elaboration of group V into V' may be unnecessary. The deprotection of compounds VII producing substances of formula III can be accomplished using conventional peptide chemistry techniques, such as employment of haloacids or trifluoracetic acid or catalytic hydrogenation.

The compounds of the invention having structural formula I may be prepared by reacting a compound of structural formula VIII with a compound of structure III in the presence of a suitable condensing agent such as dicyclohexylcarbodiimide (DCC) or arylsulfonyl chlorides such as mesitylenesulfonyl chloride or 2,4,6,-triisopropylbenzenesulfonyl chloride producing compounds of structural formula IV (R. Lohrmann and G. H. Khorana, JACS, Vol. 80, 1966, p. 829; Tsujiaki Hata and Mitsuo Sekiue, Tet. Lett. Vol 24, No. 51, p. 5741, 1983), as shown in Equation 3.

EQUATION 3

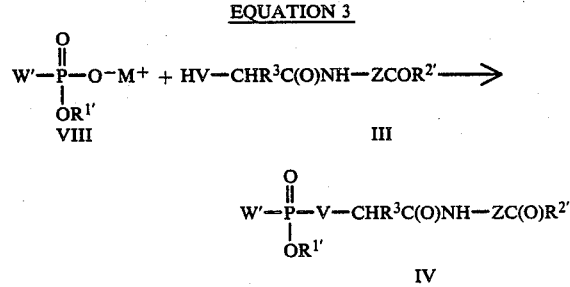

Where $M^+$ is a protonated tertiary amine, a quaternary ammonium ion such as tetrabutylammonium, an alkali earth metal cation such as lithium, sodium or potassium or a proton.

The compounds of the invention having structural formula I are synthesizable by reaction of a compound of structural formula IX with a compound of structure X to furnish a compound IV as shown in Equation 4.

EQUATION 4

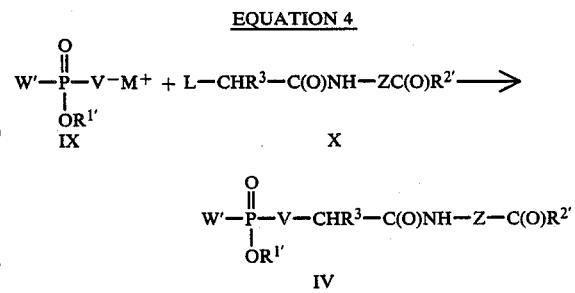

The reaction depicted in equation 4 takes place in a suitable inert solvent such as $CH_2Cl_2$, toluene, ethyl acetate or dimethyl formamide at ambient temperatures or reflux in the presence or absence of a tertiary amine base. W', $R^{1'}$, V, L, $R^3$, Z and $R^{2'}$ are defined as previously. $M^+$ is defined as previously with the added condition that it can be $Ag^+$ when V is O.

The compounds of the invention having structural formula I may be prepared by phosphorylating a compound of chemical formula XI with a compound of structure XII followed by esterification with an alcohol $R^{1'}OH$ to produce a compound of structure XIII. Esters XIII can be hydrolyzed under basic conditions and the resulting carboxylic acids can be coupled with amines XIV via standard amino acid coupling procedure to produce compounds of structure IV as shown in Equation 5.

EQUATION 5

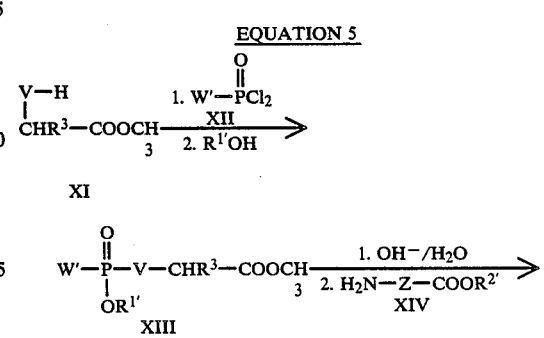

EQUATION 5

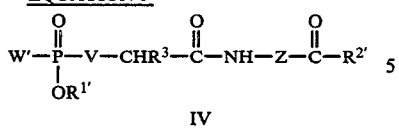

IV

Where V, $R^3$, $R^{1'}$, W' and $R^{2'}$ have the meaning as herein defined.

A number of compounds represented by structural formula I may be prepared by phosphorylating a compound XI with phosphorus oxychloride followed by esterification of the resulting intermediate by sequential addition of alcohols $R^{1'}OH$ and $R^{1'''}OH$, basic hydrolysis and coupling of the resulting carboxylic acid XV with an amine XIV to produce compounds of general formula XVI as shown in Equation 6.

EQUATION 6

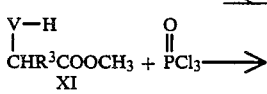
XI

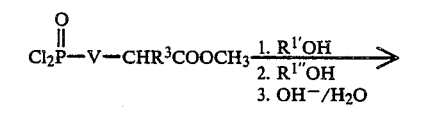

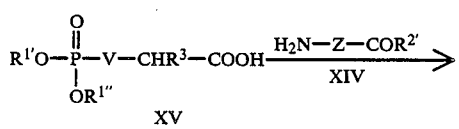
XV

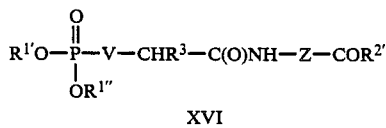
XVI

Where $R^{1'''}$ is chosen from among the groups herein defined for $R^{1'}$.

Groups W', $OR^{1'}$, $R^{2'}$ and $OR^{1'''}$ in compounds of formula IV, and XVI may be fully or partially replaced by hydroxyl furnishing compounds of structure I by using conventional chemical manipulations on properly chosen groups W', $R^{1'}$, $R^{2'}$, and $R^{1'''}$. For example, subjecting a triester such as XVII to catalytic hydrogenation furnishes the tricacid XVIII as shown in Equation 7.

EQUATION 7

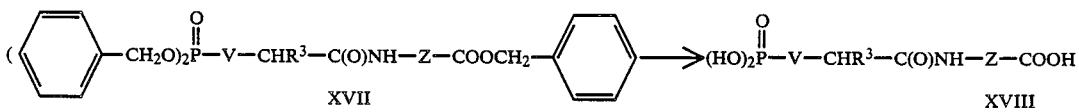

An example of replacement of a single group such as $OR^1$ by hydroxyl may be accomplished by treating a compound XIX with excess trimethylsilybromide in methylene chloride solution containing excess Proton-Sponge® as HBr scavenger to furnish a compound XX. In those cases wherein W' in structure XIX is alkoxyl, W' in structure XX will become hydroxyl.

EQUATION 8

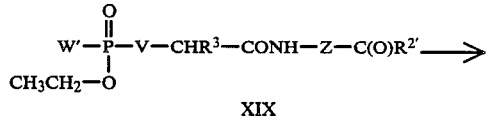
XIX

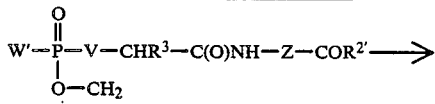
XX

Alternatively, upon catalytic hydrogenation a compound of structure XXI may furnish compounds of structure XX wherein only the single O-benzyl group has been replaced by hydroxyl, provided $R^{2'}$ and W' in structure XXI are not benzyloxyl. In the case of $R^{2'}$ and/or W' being benzyloxyl, monodebenzylation producing XX can be effected by treating a hot acetone solution of XXI with excess sodium iodide followed by acidic work-up of the reaction mixture as shown in Equation 9.

EQUATION 9

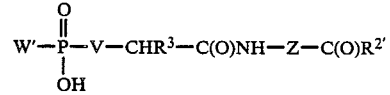
XXI

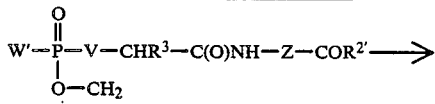
XX

One of ordinary skill in the art, will appreciate that not all of the compounds of this invention may be readily prepared by any one process. However, it is clear that by selecting a particular process from those set forth above, all of the compounds of this invention may be prepared. Further, a number of intermediates for preparing the compounds of this invention are commercially available or they may be readily prepared by art recognized methods. Intermediates for preparing the compounds of this invention are described or the preparation thereof is embodied in the following publications:

1. For the synthesis of phosphonate esters see: *Methoden Organischen Chemie, Houben-Weyl*, Vol. 12/1, 1963, p. 433–453.

2. For cleavage of phosphonate esters to phosphonate ester monohalides see: *Methoden Organischen Chemie, Houben-Weyl*, Vol. 12/1, 1963, p. 415–417.

3. For synthesis of phosphonate ester monohalides from phosphonyl halides and alcohols, see: *Methoden Organischen Chemie, Houben-Weyl*, Vol. 12/1, 1963, p. 417, 423–432.

4. For additional methods of synthesis of phosphonyl ester monochlorides see: *Methoden Organischen Chemie, Houben-Weyl*, Vol. 12/1, 1963, p. 418, 419.

5. For synthesis of phosphonyldichlorides see: *Methoden Organischen Chemie, Houben-Weyl*, Vol. 12/1, 1963, p. 387–403.

Reviews on phosphorylation

6. D. M. Brown, *Adv. in Org. Chem*, Vol. 3, p. 75.
7. *Methoden Organischen Chemie, Houben-Weyl*, Vol. 12/2, 1964.
8. Synthesis of thiophosphonate-O, S-diesters from —O— esters and alkyl halides, *Methoden Organischen Chemie, Houben-Weyl*, Vol. 12/1, 1963 p. 576–577.
9. Synthesis of thiophosphate-O, S-diesters by phosphorylation of thiols; *Methoden Organischen Chemie, Houben-Weyl*, Vol. 12/1, 1963, p. 577–579.
10. Prep. of phosphonate half esters, Chem. Ber., 93, 1220 (1960).
11. Hydrolysis of phosphonate esters, Synthesis, 409, 412 (1982).
12. Cleavage of alkyl phosphonate esters using bromotrimethylsilane, *J. Chem. Soc. Chem. Comm* 730 (1979).

The following table lists preferred compounds having structural formula I.

TABLE I

1. N-[(S)2-[(ethoxyethylphosphinyl)oxy]-1-oxo-3-phenylpropyl]β-alanine ethyl ester;
2. N-[(S)2-[(ethylhydroxyphosphinyl)oxy]-1-oxo-3-phenylpropyl]β-alanine ethyl ester, calcium salt thereof;
3. N-[(S)2-[(ethoxyethylphosphinyl)oxy]-1-oxo-3-phenylpropyl]β-alanine (phenylmethyl) ester;
4. N-[(S)2-[(ethylhydroxyphosphinyl)oxy]-1-oxo-3-phenylpropyl]β-alanine (phenylmethyl) ester, calcium salt thereof;
5. N-[(S)2-[(ethylhydroxyphosphinyl)oxy]-1-oxo-3-phenylpropyl]β-alanine, calcium salt thereof;
6. N-[(S)2-[(ethoxyphenylphosphinyl)oxy]-1-oxo-3-phenylpropyl]β-alanine ethyl ester;
7. N-[(S)2-(hydroxyphenylphosphinyl)oxy]-1-oxo-3-phenylpropyl]β-alanine ethyl ester, calcium salt thereof;
8. N-[(S)2-[(ethoxyphenylphosphinyl)oxy]-1-oxo-3-phenylpropyl]β-alanine (phenylmethyl) ester;
9. N-[(S)2-[(hydroxyphenylphosphinyl)oxy]-1-oxo-3-phenylpropyl]β-alanine (phenylmethyl) ester, calcium salt thereof;
10. N-[(S)2-[(hydroxyphenylphosphinyl)oxy]-1-oxo-3-phenylpropyl]β-alanine, calcium salt thereof;
11. N-[(S)2-[(ethoxy(phenylmethyl)phosphinyl]oxy]-1-oxo-3-phenylpropyl]β-alanine ethyl ester;
12. N-[(S)2-[[hydroxy(phenylmethyl)phosphinyl]oxy]-1-oxo-3-phenylpropyl]β-alanine ethyl ester, calcium salt thereof;
13. N-[(S)2-[[ethoxy(phenylmethyl)phosphinyl]oxy]-1-oxo-3-phenylpropyl]β-alanine (phenylmethyl) ester;
14. N-[(S)2-[[hydroxy(phenylmethyl)phosphinyl]oxy]-1-oxo-3-phenylpropyl]β-alanine (phenylmethyl) ester, calcium salt thereof;
15. N-[(S)2-[[hydroxy (phenylmethyl)phosphinyl]oxy]-1-oxo-3-phenylpropyl]β-alanine, calcium salt thereof;
16. N-[(S)2-[[ethoxy(2-phenylethyl)phosphinyl]oxy]-1-oxo-3-phenylpropyl]β-alanine ethyl ester,
17. N-[(S)2-[[hydroxy(phenylethyl)phosphinyl]oxy]-1-oxo-3-phenylpropyl]β-alanine ethyl ester, calcium salt thereof;
18. N-[(S)2-[[ethoxy(2-phenylethyl)phosphinyl]oxy]-1-oxo-3-phenylpropyl]β-alanine (phenylmethyl) ester;
19. N-[(S)2-[[hydroxy(2-phenylmethyl)phosphinyl]oxy]-1-oxo-3-phenylpropyl]β-alanine (phenylmethyl) ester, calcium salt thereof;
20. N-[(S)2-[[hydroxy(2-phenylethyl)phosphinyl]-1-oxo-3-phenylpropyl]β-alanine, calcium salt thereof;
21. N-[(S)2-[[ethoxy(3-phenylpropyl)phosphinyl]oxy]-1-oxo-3-phenylpropyl]β-alanine ethyl ester;
22. N-[(S)2-[[hydroxy(3-phenylpropyl)phosphinyl]oxy]-1-oxo-3-phenylpropyl]β-alanine ethyl ester, calcium salt thereof;

TABLE I-continued

23. N-[(S)2-[[ethoxy(3-phenylpropyl)phosphinyl]oxy]-1-oxo-3-phenylpropyl]β-alanine (phenylmethyl) ester;
24. N-[(S)2-[[hydroxy(3-phenylpropyl)phosphinyl]oxy]-1-oxo-3-phenylpropyl]β-alanine (phenylmethyl) ester, calcium salt thereof;
25. N-[(S)2-[[hydroxy(3-phenylpropyl)phosphinyl]oxy]-1-oxo-3-phenylpropyl]β-alanine, calcium salt thereof;
26. 4-[[(S)2-[(ethoxyethylphosphinyl)oxy]-1-oxo-3-phenylpropyl]amino]benzoic acid ethyl ester,
27. 4-[[(S)2-[(ethylhydroxyphosphinyl)oxy]-1-oxo-3-phenylpropyl]amino]benzoic acid ethyl ester, calcium salt thereof;
28. 4-[[(S)2-[(ethoxyethylphosphinyl)oxy]-1-oxo-3-phenylpropyl]amino]benzoic acid (phenylmethyl) ester;
29. 4-[[(S)2-[(ethylhydroxyphosphinyl)oxy]-1-oxo-3-phenylpropyl]amino] benzoic acid phenylmethyl ester, calcium salt thereof;
30. 4-[[(S)2-[(ethoxylhydroxyphosphinyl)oxy]-1-oxo-3-phenylpropyl]amino] benzoic acid, calcium salt thereof, calcium salt thereof;
31. 4-[[(S)2-[[ethoxy(2-phenylethyl)phosphinyl]oxy]-1-oxo-3-phenylpropyl]amino] benzoic acid ethyl ester;
32. 4-[[(S)2-[[hydroxy(2-phenylethyl)phosphinyl]oxy]-1-oxo-3-phenylpropyl]amino] benzoic acid methyl ester, calcium salt thereof;
33. 4-[[(S)2-[[ethoxy(2-phenylethyl)phosphinyl]oxy]-1-oxo-3-phenylpropyl]amino] benzoic acid (phenylmethyl) ester;
34. 4-[[(S)2-[[hydroxy(2-phenylethyl)phosphinyl]oxy]-1-oxo-3-phenylpropyl]amino] benzoic acid (phenylmethyl)ester, calcium salt thereof;
35. 4-[[(S)2-[[hydroxy(2-phenylmethyl)phosphinyl]oxy]-1-oxo-3-phenylpropyl]amino] benzoic acid, calcium salt thereof;
36. N-[(S)2-[(dimethoxyphosphinyl)oxy]-1-oxo-3-phenylpropyl]β-alanine ethyl ester;
37. N-[(S)2-[(phosphonoxy)-1-oxo-3-phenylpropyl]β-alanine ethyl ester, calcium salt thereof;
38. N-[(S)2-[(dimethoxyphosphinyl)oxy]-1-oxo-3-phenylpropyl]β-alanine (phenylmethyl) ester;
39. N-[(S)2-[(phosphonoxy)-1-oxo-3-phenylpropyl]β-alanine (phenylmethyl) ester, calcium salt thereof;
40. N-[(S)2-[(phosphonoxy)-1-oxo-3-phenylpropyl]β-alanine, calcium salt thereof;
41. 4-[[(S)2-[(dimethoxyphosphinyl)oxy]-1-oxo-3-phenylpropyl]amino] benzoic acid ethyl ester;
42. 4-[[(S)2-(phosphonooxy)-1-oxo-3-phenylpropyl]amino benzoic acid ethyl ester, calcium salt thereof;
43. 4-[[(S)2-[(dimethoxyphosphinyl)oxy]-1-oxo-3-phenylpropyl]amino] benzoic acid (phenylmethyl) ester;
44. 4-[[(S)2-(phosphonooxy)-1-oxo-3-phenylpropyl]amino] benzoic acid (phenylmethyl) ester, calcium salt thereof;
45. 4-[[(S)2-(phosphonooxy)-1-oxo-3-phenylpropyl]amino] benzoic acid, calcium salt thereof;
46. N-[(S)2-[[bis(phenylmethoxy)phosphinyl]oxy]-1-oxo-3-phenylpropyl]β-alanine ethyl ester;
47. N-[(S)2-[[hydroxy (phenylmethoxy)phosphinyl]oxy]-1-oxo-3-phenylpropyl]β-alanine ethyl ester, calcuim salt thereof;
48. N-[(S)2-[[bis(phenylmethoxy)phosphinyl]oxy]-1-oxo-3-phenylpropyl]β-alanine (phenylmethyl) ester;
49. N-[(S)2-[[hydroxy(phenylmethyl)phosphinyl]oxy]-1-oxo-3-phenylpropyl]β-alanine (phenylmethyl) ester, calcium salt thereof;
50. N-[(S)2-[[hydroxy(phenylmethoxy)phosphinyl]oxy]-1-oxo-3-phenylpropyl]β-alanine, calcium salt thereof;
51. N-[(S)2-[[methoxy(2-phenylethoxy)phosphinyl]oxy]-1-oxo-3-phenylpropyl]β-alanine ethyl ester;
52. N-[(S)2-[[hydroxy(2-phenylmethoxy)phosphinyl]oxy]-1-oxo-3-phenylpropyl]β-alanine ethyl ester, calcium salt thereof;
53. N-[(S)2-[[methoxy(2-phenylethoxy)phosphinyl]oxy]-1-oxo-3-phenylpropyl]β-alanine (phenylmethyl) ester;
54. N-[(S)2-[[hydroxy(2-phenylethoxy)phosphinyl]oxy]-1-oxo-3-phenylpropyl]β-alanine (phenylmethyl) ester, calcium salt thereof;
55. N-[[(S)2-[[hydroxy(2-phenylethoxy)phosphinyl]oxy]-1-oxo-3-phenylpropyl]β-alanine, calcium salt thereof;
56. 4-[[(S)2-[[bis(phenylmethoxy)phosphinyl]oxy]-1-oxo-3-phenylpropyl]amino] benzoic acid ethyl ester;
57. 4-[[(S)2-[[hydroxy(phenylmethyl)phosphinyl]oxy]-1-

TABLE I-continued oxo-3-phenylpropyl]amino] benzoic acid ethyl ester, calcium salt thereof;

58. 4-[[(S)2-[[bis(phenylmethoxy)phosphinyl]oxy]-1-oxo-3-phenylpropyl]amino]benzoic acid (phenylmethyl) ester;
59. 4-[[(S)2-[[hydroxy(2-phenylmethoxy)phosphinyl]oxy]-1-oxo-3-phenylpropyl]benzoic acid phenylmethyl ester, calcium salt thereof;
60. 4-[[(S)2-[[hydroxy(phenylmethoxy)phosphinyl]oxy]-1-oxo-3-phenylpropyl amino]benzoic acid, calcium salt thereof;
61. 4-[[(S)2-[[methoxy(phenylethoxy)phosphinyl]oxy]-1-oxo-3-phenylpropyl]amino] benzoic acid ethyl ester;
62. 4-[[(S)2-[[hydroxy(2-phenylethoxy)phosphinyl]oxy]-1-oxo-3-phenylpropyl]amino]benzoic acid ethyl ester, calcium salt thereof;
63. 4-[[(S)2-[[methoxy(2-phenylethoxy)phosphinyl]oxy]-1-oxo-3-phenylpropyl]amino]phenylmethyl ester;
64. 4-[[(S)2-[[hydroxy (2-phenylethoxy)phosphinyl]oxy]-1-oxo-3-phenylpropyl]amino]benzoic acid (phenylmethyl) ester, calcium salt thereof; and
65. 4-[[(S)2-[[hydroxy(2-phenylethoxy)phosphinyl]oxy]-1-oxo-3-phenylpropyl]amino]benzoic acid, calcuim salt thereof.

As used herein, unless stated otherwise, the terms alkyl and alkoxy denote such groups having straight or branched carbon chains of from 1 to 6 carbon atoms and the term halogen denotes fluorine, chlorine, bromine and iodine.

Compounds having structural formula I wherein $R^1$ is hydrogen and/or $R^2$ is hydroxy form salts with pharmaceutically acceptable bases. Sodium, potassium and calcium hydroxide as well as sodium and potassium carbonate are examples of suitable bases for this purpose. In addition, salts formed with pharmaceutically acceptable amines such as for example ammonia, N-methyl glucamine, ethanolamine, diethanolamine, lysine and arginine are also contemplated.

Certain of the compounds of the invention form solvates with, for example, pharmaceutically acceptable solvents such as water and ethyl alcohol. Such solvates are considered to be equivalent to the corresponding nonsolvated molecules for purposes of the invention.

In formula I, certain atoms may be asymmetric (chiral) centers. Such centers will be readily apparent to those skilled in the art. The invention contemplates all isomers at these centers both in pure form and in admixture.

The compounds having structural formula I inhibit the activity of enzymes designated enkephalinases. The compounds are particularly useful for the inhibition of enkephalinase A.

The following test procedure is utilized to assay the enkephalinase A inhibition of the compounds having structural formula I.

Enkephalin (ENK) degrading activity is separated into the following three fractions according to the method of Gorenstein and Snyder, (Life Sci., 25, 2065 (1979)]: Enk'ase A ($Gly^3$-$Phe^4$), Aminopeptidase, (AP) ($Tyr^1$-$Gly^2$), and Enk'ase B ($Gly^2$-$Gly^3$).

Enzyme activity is separated by taking the brain tissue (minus cerebellum) from Sprague-Dawley rats and homogenizing it in 30 volumes of 50 mM Tris buffer, pH 7.4, using a Brinkmann Polytron. The resulting homogenate is centrifuged at 50,000×g for 15 min. The pellet, constituting the membrane bound enzyme material, is washed by resuspending it in Tris and re-centrifuging it 4 times.

Following washing, solubilization of the membrane pellet is achieved by incubating it for 45 min at 37° C. in the presence of 15 volumes (based on initial brain weight) of 50 mM Tris-1% Triton X-100 buffer, pH 7.4. After centrifugation at 100,000×g for 60 minutes to remove non-solubilized material, the Triton soluble supernatant is layered on a 1.5×30 cm DEAE Sephacel column previously equilibrated with 50 mM Tris-0.1% Triton, pH 7.4. Material is eluted from the column using a 1 liter linear NaCl gradient running from 0.0 to 0.4M. Effluent is collected in 7 ml fractions, each of which is assayed for enkephalin degrading activity. Under these conditions Enk'ase A activity is found to elute between 120 and 200 ml. followed by AP activity (260 to 400 ml) and finally by Enk'ase B activity between 420 and 450 ml.

Enkephalin degrading activity is monitored using a radiometric assay. The substrate is $^3$H-$Met^5$-ENK (50.1 Ci/mmol, New England Nuclear) diluted in 0.05M Tris buffer, pH 7.4, such that the final reaction mixture concentration is 40 nM. Total reaction mixture volume including enzyme and substrate is 250 ul. Incubation is carried out for 90 min at 37° C. To stop the reaction, tubes are transferred to a boiling water bath for 15 min.

Assay products are separated from one another using thin layer chromatography. A 4 ul aliquot of the reaction mixture is spotted on a Baker-flex Silica Gel 1B plate (20×20 cm) along with unlabeled standards ($Met^5$-ENK, tyrosine, tyrosylglycine, tyrosyl-glycyl-glycine) and the components co-chromatographed in an isopropanol:ethyl acetate: 5% acetic acid solvent system (2:2:1) which is capable of resolving $Met^5$-ENK from its breakdown products. Total running time is approximately 17 hours. TLC tanks are gassed with nitrogen prior to starting the run. Following the run, markers are visualized with ninhydrin spray. These spots, along with remaining plate regions, are cut from the plate and the radioactivity corresponding to each monitored using liquid scintillation counting. $IC_{50}'s$ are determined using linear regression techniques.

The following test procedure is utilized to assess the potentiatiation of the analgesic effects of (D-$Ala^2$-$Met^5$)-enkephalinamide (DAEAM) by the compounds of this invention. Background for the use of this procedure is given in Chipkin, R. E., Iorio, L. C., Barnett, A., Berger, J., and Billard, W., *Regulatory Peptides: From Molecular Biology to Function*, edited by E. Costa and M. Trabucchi, Raven Press, New York, 1982 pp. 235–242.

Male CF1 mice (19–23 g) from Charles River Breeding Labs, Mass., are used (N=10/dose or does combination). Tailflick testing is done similar to that of Dewey and Harris, *Methods in Narcotic Research*, Eds., S. Ehrenpreis and A. Neidle, pp. 101–109, Marcel Dekker, Inc., New York, 1975 using a radiant heat noxious stimulus. following determination of control latencies (typically 2–3 sec), the mice are first injected (sc or po) with either vehicle or drug and after an appropriate interval injected intracerebroventricularly (icv) with either vehicle (10 ul of saline) or DAEAM according to haley and McCormick, *Br. J. Pharmaceol.*, 12, 12 (1957). Tailflick latencies are re-determined 30 min later, as this has previously been determined to be the time of peak analgesia for DAEAM, a cut-off of 10 sec is employed.

Utilizing this procedure, parenteral and/or oral $ED_{50}$ values (the dose at which half the test animals displayed analgesia) can be obtained for compounds having structural formula I.

The compounds having structural formula I may be utilized to exert their analgesic effect in the many dosage forms known to the art, such as tablets, capsules or elixirs for oral administration or in sterile solutions or suspensions for parenteral administration. The foregoing pharmaceutical dosage forms are advantageously prepared using, in addition to a compound of this invention, pharmaceutically acceptable and compatible excipients, binders, preservatives, stabilizers, flavors and the like. In each of the dosage forms the active compound will be administered in a dosage in the range of from about 0.01 to about 200 m.p.k. A more preferred dosage range is from about 0.1 to about 50 m.p.k. The doses are to be administered at intervals of from 3 to 8 hours. However, the quantity and frequency of dosage will depend upon such factors as the severity of the pain, the general physical condition of the patient, including the age and weight of the patient and other factors which a person skilled in the art will recognize.

The mechanism whereby the compounds of the invention exert their analgesic effect is not completely understood. It is believed that this effect may be due at least in part to the compound's inhibitory effect on the action of enkephalinases, which effect has been demonstrated.

The chemical names of those compounds designated by number in the following preparative examples are listed in Table I.

EXAMPLE 1

N-(S)-phenyllactoyl)β-alanine ethyl ester

To a solution of 1.0 g (6.02 mmoles) of S-phenyllactic acid, 18.5 g (12.04 mmoles) of 1-hydroxybenzotriazole, 0.92 g (6.02 mmoles) of β-alanine ethyl ester hydrochloride and 1.618 (14 mmoles) of N-ethylmorpholine in 20 mL of dry N,N-dimethyl formamide at ice bath temperature under a nitrogen atmosphere add 1.16 g (6.02 mmoles) of 1-(3-dimethylaminopropyl)-3-ethyl carbodiimide hydrochloride, remove the ice bath and stir the resulting mixture at room temperature for 15 hr. Dilute the reaction mixture with 75 mL of ethyl acetate and wash with saturated NaHCO$_3$ solution (100 ml), 1N citric acid (100 ml), NaHCO$_3$ solution (100 ml), saturated NaCl solution (100 ml) and dry the organic layer over NaSO$_4$. Evaporate the dried organic phase to an oil in vacuo and purify the product isolated by flash chromatography [J. Org. Chem., 43, 2923 (1978)]on SiO$_2$, to isolate the title dipeptide as a colorless oil.

Use the same procedure, substituting β-alanine ethyl ester hydrochloride with β-alanine benzyl ester hydrochloride, p aminobenzoic acid ethyl ester hydrochloride, or p-aminobenzoic acid benzyl ester hydrochloride to synthesize N-(S)-phenyllactoyl) β-alanine benzyl ester, N-(S)-phenyllactoyl)-p-aminobenzoic acid ethyl ester or N-(S)-phenyllactoyl)-p-aminobenzoic acid benzyl ester.

EXAMPLE 2

N-[(S)2-[(ethoxyethyl phospinyl)oxy]-1-oxo-3-phenylpropyl]β-alanine ethyl ester

A. Prepare ethyl ethylphosphonochloridate by dissolving 2.0 g (12.05 mmoles) of ethyl diethylphosphonate in dry benzene (20 ml) containing 2.71 g PCl$_5$ (13.0 mmole) and refluxing the resulting solution for 50 min under Argon. Cool the reaction mixture to room temperature, evaporate to dryness in vacuo, dissolve the residue in dry tetrahydrofuran (10 ml) and add the solution to a stirred ice-cooled solution of 3.31 g N-(S)-phenyllactoyl) β-alanine ethyl ester in dry pyridine (5 ml) under Argon. Stir the resulting mixture at 0°-5° C. for 1 hour and at room temperature for 15 hrs. Dilute the reaction mixture with 100 ml of ethyl acetate and wash the solution with water (3×100 ml), saturated NaHCO$_3$ solution (3×100 ml), water (3×100 ml), 1.0M HCl (3×100 ml), saturated NaHCO$_3$ solution (2×100 ml), brine (1×100 ml) and dry over Na$_2$SO$_4$. Evaporate the solvent to dryness and obtain the crude product of this example. Purify by the flash chromatography over SiO$_2$.

Use the same procedure substituting N-(S)-phenyllactoyl) β-alanine ethyl ester with N-(S)-phenyllactoyl) β-alanine benzyl ester, N-(S)-phenyllactoyl) p-amino benzoic acid ethyl ester or N-(S)-phenyllactoyl) p-amino benzoic acid benzyl ester to synthesize compounds 3, 26 or 28.

Use the same procedure substituting ethyl ethylphosphonochloridate with the appropriate aralkyl ethylphosphonochloridate or phenyl ethyl-phosphonochloridate and when necessary substituting N-(S)-phenyllactoyl) β-alanine ethyl ester with N-(S)-phenyllactoyl) β-alanine benzyl ester, N-(S)-phenyllactoyl) p-aminobenzoic acid ethyl ester or N-(S)-phenyllactoyl) p-aminobenzoic acid benzyl ester and synthesize compounds 3, 6, 8, 11, 13, 16, 18, 21, 23, 31 or 33.

EXAMPLE 3

N-[(S)2-[(ethylhydroxyphospinyl)oxy]-1-oxo-3-phenylpropyl]b-alanine ethyl ester

To a solution of 1.5 g of N-[(S)2-[(ethoxyethylphosphinyl)oxy]1-oxo-3-phenylpropyl]b-alanine ethyl ester (3.70 mmoles) in dry methylene chloride (8 ml) containing 70.65 g of Proton-Sponge ® (4.50 mmoles), under argon at ice-bath temperature add 1.57 ml bromotrimethylsilane (12.0 mmoles) and stir the resulting mixture at room temperature for 3 hours. Filter the reaction mixture rapidly, washing the precipitate with methylene chloride (5×8 ml) and evaporate the pooled filtrate and washings to dryness in vacuo. Dissolve the oily residue in 10 ml of dry ethyl acetate and evaporate to dryness in vacuo. Repeat this procedure three times and dissolve the product in acetone (15 ml) to which water (3 ml) is added. Stir the resulting solution for 10 min., evaporate it to dryness in vacuo and purify the product of this example isolated by flash chromatography on SiO$_2$.

Use the same procedure substituting 3, 6, 8, 11, 13, 16, 18, 21, 23, 26, 28, 31 or 33 for 1 and synthesize compounds 4, 7, 9, 12, 14, 17, 19, 22, 24, 27, 29, 32 or 34.

EXAMPLE 4

N-[(S)2-[(ethylhydroxyphosphinyl)oxy]-1-oxo-3-phenylpropyl]b-alanine

To a solution of 1.0 g of N-[(S)2-[(ethylhydroxyphosphinyl)oxy]-1-oxo-3-phenylpropyl]b-alanine phenylmethyl ester in 15 ml of absolute ethanol, add 100 mg of 10% Pd on Carbon and hydrogenate the mixture on a Parr hydrogenator at 50 psi of hydrogen pressure for 3 hrs. Filter the reaction mixture, washing the catalyst with 5 ml of ethanol and evaporate the combined filtrate and washings to dryness in vacuo and isolate the diacid N-[(S)2-[(ethylhydroxyphosphinyl)oxy]-1-oxo-3-phenylpropyl]β-alanine.

Form the calcium salt of N-[(S)2-[(ethylhydroxyphosphinyl)oxy]-1-oxo-3-phenylpropyl]β-alanine by dissolving 0.5 g (1.52 mmoles) of the diacid in 50 ml of hot water containing 112.5 mg (1.52 mmoles) of calcium hydroxide under argon and stirring the resulting mixture vigorously for 3 hrs. Filter the cloudy solution and evaporate the filtrate to dryness in vacuo and isolate the product of this example as a white solid. Suspend the white product in ethanol and filter. Dry the calcium salt of N-[(S)2-[(ethylhydroxyphosphinyl)oxy]-1-oxo-3-phenylpropyl]β-alanine in high vacuum over $P_2O_5$.

Use the same procedure substituting 9, 14, 19, 24, 29 or 34 for 4 and synthesize compounds 10, 15, 20, 25, 30 or 35.

EXAMPLE 5

N-[(S)2-[(dimethoxyphosphinyl)oxy]-1-oxo-3-phenylpropyl]β-alanine ethyl ester

Procedure A:

Prepare N-[(S)2-[(dimethoxyphosphinyl)oxy]-1-oxo-3-phenylpropyl-β-alanine ethyl ester following the procedure in Example 2 by substituting ethyl ethylphosphonochloridate with dimethylphosphorochloridate and purify the crude product isolated by flash chromatography on $SiO_2$.

Procedure B:

Carry out the phosphorylation of (S)-N-phenyllactoyl β-alanine ethyl ester with dimethylphosphorochloridate as described above and in example 2 but in the presence of 10%-mol of 4-dimethylaminopyridine.

Use the same procedures substituting N-(S)-phenyllactoyl)β-alanine ethyl ester with N-(S)-phenyllactoyl)β-alanine benzyl ester, N-(S)-phenyllactoyl)-p-aminobenzoic acid ethyl ester or N-(S)-phenyllactoyl)-p-aminobenzoic acid benzyl ester and when necessary substitute dimethyl chlorophosphate with phenethylmethyl chlorophosphate to synthesize 41, 43, 51, 53, 61 or 63.

EXAMPLE 6

N-[(S)2-[(phosphonooxy)-1-oxo-3-phenylpropyl]β-alanine ethyl ester

Starting with 5 moles of N-[(S)2-[(dimethoxyphosphinyl)-1-oxo-3-Phenylpropyl]β-alanine ethyl ester, 5.1 mmoles of Proton Sponge ® and 25 mmoles of bromotrimethylsilane in 10 ml of dry methylene chloride prepare N-[(S)2-[(phosphonooxy)-1-oxo-3-phenylpropyl]β-alanine ethyl ester following the procedure of Example 3.

Use the same procedure with 38, 41, 43, 51, 53, 61 or 63 to synthesize 39, 42, 44, 52, 54, 62 or 64.

EXAMPLE 7

N-[(S)2-[(phosphonooxy)-1-oxo-3-phenylpropyl]β-alanine

Prepare N-[(S)2-[(phosphonooxy)-1-oxo-3-phenylpropyl]β-alanine by hydrogenating 1.0 g of N-[(S)2-[(phosphonooxy)-1-oxo-3-phenylpropyl]β-alanine phenylmethyl ester in 15 ml of absolute ethanol as described in Example 4.

Prepare the calcium salt of N-[(S)2-[(phosphonooxy)-1-oxo-3-phenylpropyl]β-alanine using 1.5 equivalents of Ca(OH)$_2$ and 1.0 equivalents of N-[(S)2-[(phosphonooxy)-1-oxo-3-phenylpropyl]β-alanine by following the procedure in example 4.

Use the above procedure substituting 39 with 44, 54, or 64 and prepare compounds 45, 55 or 65.

EXAMPLE 8

(S)-α-[[Bis-(phenylmethoxy)phosphinyl]benzenepropanoic acid

To a stirred, ice-cold solution of 3.4 ml (36.7 mmole) of phosphorous oxychloride in 37 ml of dry THF (tetrahydrofuran) in a flame-dried flask under nitrogen add 5.4 ml (66 mmole) of dry pyridine. Add (S)-phenyllactic acid methyl ester (6.0 g, 33.3 mmole) in 33 ml of dry THF dropwise to the reaction mixture over a period of 1 hr. Stir the resulting suspension for an additional 20 min and add to it dropwise at 0° C. 7.6 ml (73 mmole) of benzyl alcohol and 8.05 ml of dry pyridine in 40 ml of THF. Stir the reaction mixture at room temperature overnight and filter. Wash the precipitated pyridinium hydrochloride with ethyl acetate (3×10 ml) and evaporate the pooled filtrates and washings to dryness in vacuo. Dissolve the residue in 50 ml of ethyl acetate and wash with ice-cold 1% $H_2SO_4$ solution (3×50 ml), water (3×50 ml), conc. sodium bicarbonate solution (3×50 ml), water (3×50 ml) and brine (1×50 ml). Dry over sodium sulfate, evaporate to dryness in vacuo and purify the resultant yellow oil by flash chromatography (12×15.5 cm column, ethyl acetate/hexane, 1/3). Isolate the (S)-α-[[bis-(phenylmethoxy)phosphinyl]benzenepropanoic acid as a colorless oil, 2.815 g, $[\alpha]_D^{26}=-11.8°(C=1, CH_3OH)$ Anal. Calcd C: 65.46%, H: 5,68%, P: 7.04%, Found: C: 65.27%, H: 5.57%, P: 6.87%.

To a stirred solution of 1.96 g (4.45 mmole) of S-α-[bis-(phenylmethoxy)phosphinyl]benzenepropanoic acid methyl ester in 3 ml of methanol add sequentially 800 ul of water, 2.40 ml of 2.0M potassium hydroxide and 3 ml of water at ice-bath temperature. Stir the resulting mixture at room temperature for 50 hrs and then dilute with 25 ml of water. Concentrate to about 10 ml, dilute with 60 ml of water and wash with ethyl acetate (4×50 ml). Adjust the pH of the aqueous phase to 2 using cold 2% sulfuric acid, filter the resulting precipitate, wash with water (10×10 ml) and dry over $P_2O_5$ in vacuo. Isolate 0.911 g of the product of this example as colorless plates, mp 123°-124° C., $[\alpha]_D^{26}=-19.0°$ (C=1 $CH_3OH$), Anal. Calcd: C: 64.79%, H: 5.40%, P: 7.27%, Found: C: 64.47%, H: 5.31%, P: 7.27%.

Use the above phosporylation procedure followed by the hydrolysis reaction substituting benzyl alcohol with methanol or sequentially added 1.10 equivalents of methanol and 1.10 equivalents of phenethylalcohol and prepare (S)-α-[(dimethoxyphosphinyl)benzenepropanoic acid or (S)-α-[[methoxy(2-phenylethoxyl)phosphinyl]oxy]-3-phenylpropanoic acid.

Use the above procedure substituting phosphorous oxychloride with ethyldichlorophosphonate, phenyldichlorophosphonate, benzyldichlorophosphonate or phenethyldichlorophosphonate and benzyl alcohol with ethanol and prepare: (S)-α-[(ethoxy)ethylphosphinyl]benzenepropanoic acid, (S)-α-[(ethoxy)phenylphosphinyl]benzenepropanoic acid, (S)-α-[ethoxy(phenylmethyl)phosphinyl]benzenepropanoic acid or (S)-α-[ethoxy(2-phenylethyl)phosphinyl]benzenepropanoic acid.

EXAMPLE 9

N-[(S)-2-[bis(phenylmethoxy)phosphinyl]oxy]-1-oxo-3-phenylpropyl]β-alanine(phenylmethyl) ester Prepare N-[(S)-2-[bis(phenylmethoxy)phosphinyl]oxy]-1-oxo-3-phenylpropyl]β-alanine phenylmethyl ester by coupling 368.7 mg (0.866 mmole) of (S)-α-[bis-(phenylmethoxy)phosphinyl]benzenepropanoic acid with 304.2 mg alanine benzyl ester p-toluenesulfonate according to the directions in Example 1 and isolate 432.7 mg of N-[(S)-2-[bis(phenylmethoxy)-phosphinyl]oxy]-1-oxo-3-phenylpropyl]β-alanine-(phenylmethyl)ester as colorless crystals mp 65°–66° C. Anal. Cald. C: 67.47%, H: 5.79%, N: 2.39%, P: 5.28%, Found: C: 67.35%, H: 5.47%, N: 2.27%, P: 5.45%.

Use the same procedure substituting β-alanine benzyl ester with β-alanine ethyl ester p-aminobenzoic acid ethyl ester or p-aminobenzoic acid benzyl ester and synthesize compounds 46, 56 and 58.

Use the above procedure substituting (S)-α-[bis-(phenylmethoxy)phosphinyl]benzenepropanoic acid with (S)-α-(dimethoxyphosphinyl)benzenepropanoic acid or (S)-α-[methoxy(2-phenylethoxy)phosphinyl]benzenepropanoic acid and when necessary β-alanine benzyl ester with β-alanine ethyl ester, p-aminobenzoic acid ethyl ester or p-aminobenzoic acid benzyl ester and prepare compounds 36, 38, 41, 43, 51, 53, 61 and 63.

Use the same procedure substituting (S)-α-[bis-(phenylmethoxy)phosphinyl]benzenepropanoic acid with (S)-α-[(ethoxy)ethylphosphinyl]benzenepropanoic acid, (S)-α-[(ethoxy)phenylphosphinyl]benzenepropanoic acid, (S)-α-[ethoxy(phenylmethyl)phosphinyl]benzenepropanoic acid or (S)-α-[ethoxy(2-phenylethyl)phosphinyl]benzenepropanoic acid or (S)-α-[ethoxy(3-phenylpropyl)phosphinyl]benzenepropanoic acid and when necessary β-alanine benzyl ester with β-alanine ethyl ester, p-aminobenzoic acid ethyl or p-aminobenzoic acid benzyl ester and prepare compounds 1, 3, 6, 8, 11, 13, 16, 18, 21, 23, 26, 28, 31 and 33.

EXAMPLE 10

N-[(S)2-phosphonooxy)-1-oxo-3-phenylpropyl]β-alanine ethyl ester

Prepare N-[(S)2-(phosphonooxy)-1-oxo-3-phenylpropyl]β-alanine ethyl ester by hydrogenolyzing 1.0 g of 46 in 15 ml of abs. ethanol containing 150 mg of Pd/C (10%) according to the directions outlined in Example 4.

Prepare 40 by substituting 46 with 48.

EXAMPLE 11

N-[(S)2-[hydroxy(phenylmethoxy)phosphinyl]oxy]-1-oxo-3-phenylpropyl]β-alanine ethyl ester Procedure A Add 10 mmoles of 46 in 10 ml of dry ethoxyethanol containing 30 mmoles of anh. lithium chloride and heat the resulting solution under argon at 100° C. for 2 hours. Evaporate the cooled reaction mixture to dryness in vacuo, dissolve the residue in water (4 ml.) adding a little methanol to obtain a homogenous mixture and acidify the solution with 1% $H_2SO_4$ to pH 0.5–1.0. Extract this solution with ethyl acetate (5×50 ml), wash the pooled extracts with water (2×150 ml), brine and dry over $Na_2SO_4$. Remove the solvent in vacuo to furnish the N-[(S)-2-[hydroxy(phenylmethoxy)phosphinyl]oxy]-1-oxo-3-phenylpropyl]β-alanine ethyl ester which is purified further by flash chromatography over $SiO_2$.

Use the same procedure substituting 46 with 48, 56, or 58 and prepare 49, 57 or 59.

Procedure B

Add 10 mmoles of 46 in 10 ml of dry acetone containing 20 mmole of NaI and reflux the resulting solution under argon for 10 hrs. Filter the reaction mixture and wash the precipitate with four 10 ml portions of hot acetone isolating the sodium salt of N-[(S)2-[hydroxy(phenylmethoxy)phosphinyl]oxy]-1-oxo-3-phenylpropyl]β-alanine ethyl ester. Dissolve the monosodium salt in 40 ml water, acidify the solution with 1% $H_2SO_4$ to pH 0.5–1.0, extract the solution with ethyl acetate (5×50 ml), dry the pooled extracts with a brine wash (1×100 ml) and over $Na_2SO_4$, evaporate to dryness in vacuo and purify the residue by flash chromatography over $SiO_2$ to isolate N-[(S)2-[hydroxy(phenylmethoxy)phosphinyl]oxy]-1-oxo-3-phenylpropyl]β-alanine ethyl ester.

EXAMPLE 12

N-[(S)-2-[hydroxy(phenylmethoxy)phosphinyl]oxy]-1-oxo-3-phenylpropyl]β-alanine

Stir a solution of 10 mmole of 47 and 12 mmole of KOH in 10 ml of 85% aq. methanol at room temperature for 48 hours under argon. Concentrate the reaction mixture to dryness, dissolve the residue in 20 ml of water, extract the aq. solution with ethyl acetate (2×20 ml), concentrate the aqueous phase to 2 ml, load the solution onto an ion-exchange resin column (2×40 cm) containing Dowex 50WX8 and elute with water. Concentrate the product containing fractions to dryness to isolate 50.

Prepare 60 substituting 47 with either 57 or 59, using the above procedure with the following modifications. Use 14 mmole of KOH and after stirring the reaction mixture at room temperature for 48 hours heat it at 60° C. for 7 hours.

We claim:

1. A compound having the structural formula I:

W—P(O)OR$^1$—V—CHR$^3$—C(O)—NH—Z—C(O)R$^2$ or a pharmaceutical acceptable salt thereof, wherein:
R$^1$ is hydrogen, methyl, ethyl, phenyl, benzyl, phenylethyl or —CR$^{11}$HOC(O)R$^{12}$ wherein R$^{11}$ and R$^{12}$ are each independently alkyl having from 1 to 6 carbon atoms or cycloalkyl having from 5 to 7 carbon atoms;
R$^2$ is hydroxy, methoxy, ethoxy, propoxy, phenylmethoxy, phenoxyethyloxy, pivaloyloxymethyloxy, —OCH$_2$CHOHCH$_2$OH or —OCH$_2$—CH——CH$_2$;
      |      |
      O      O
       \\   /
       C
      /  \\
   CH$_3$  CH$_3$ W is hydroxy, alkoxy having 1 to 6 carbon atoms, phenylmethoxy, alkyl having from 1 to 6 carbon atoms or —(CH$_2$)$_n$—⟨phenyl⟩—A {wherein n' is an integer of from 0–6, and A is hydrogen, fluorine or chlorine};
VC*HR$^3$ contains an asymmetric carbon (C*) the chirality of which is the S absolute configuration wherein V is oxygen or sulfur and wherein R$^3$ is

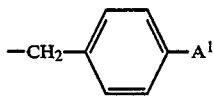

wherein $A^1$ is hydrogen, fluorine, chlorine or trifluoromethyl; and

Z is p-phenylene.

2. A compound defined in claim 1 wherein $R^1$ is hydrogen or $-CHR^{11}OC(O)R^{12}$ wherein $R^{11}$ and $R^{12}$ are defined in claim 1.

3. A compound defined in claim 1 wherein $R^2$ is hydroxy, methoxy, ethoxy, propoxy, phenoxyethyloxy, pivaloyloxymethoxy, or

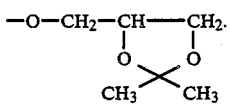

4. A compound defined in claim 1 wherein W is hydroxy.

5. A compound defined in claim 1 having the name:
4-[[(S)2-[(ethoxyethylphosphinyl)oxy]-1-oxo-3-phenylpropyl]amino]benzoic acid ethyl ester;
4-[[(S)2-[(ethylhydroxyphosphinyl)oxy]-1-oxo-3-phenylpropyl]amino]benzoic acid ethyl ester, calcium salt thereof;
4-[[(S)2-[(ethoxyethylphosphinyl)oxy]-1-oxo-3-phenylpropyl]amino]benzoic acid (phenylmethyl) ester;
4-[[(S)2-[(ethylhydroxyphosphinyl)oxy]-1-oxo-3-phenylpropyl]amino]benzoic acid phenylmethyl ester, calcium salt thereof;
4-[[(S)2-[(ethoxylhydroxyphosphinyl)oxy]-1-oxo-3-phenylpropyl]amino]benzoic acid, calcium salt thereof, calcium salt thereof;
4-[[(S)2-[[ethoxy(2-phenylethyl)phosphinyl]oxy]-1-oxo-3-phenylpropyl]amino]benzoic acid ethyl ester;
4-[[(S)2-[[hydroxy(2-phenylethyl)phosphinyl]oxy]-1-oxo-3-phenylpropyl]amino]benzoic acid methyl ester, calcium salt thereof;
4-[[(S)2-[[ethoxy(2-phenylethyl)phosphinyl]oxy]-1-oxo-3-phenylpropyl]amino]benzoic acid (phenylmethyl) ester;
4-[[(S)2-[[hydroxy(2-phenylethyl)phosphinyl]oxy]-1-oxo-3-phenylpropyl]amino]benzoic acid (phenylmethyl)ester, calcium salt thereof;
4-[[(S)2-[[hydroxy(2-phenylmethyl)phosphinyl]oxy]-1-oxo-3-phenylpropyl]amino]benzoic acid, calcium salt thereof;
4-[[(S)2-[(dimethoxyphosphinyl)oxy]-1-oxo-3-phenylpropyl]amino]benzoic acid ethyl ester;
4-[[(S)2-(phosphonooxy)-1-oxo-3-phenylpropyl]amino benzoic acid ethyl ester, calcium salt thereof;
4-[[(S)2-[(dimethoxyphosphinyl)oxy]-1-oxo-3-phenylpropyl]amino]benzoic acid (phenylmethyl) ester;
4-[[(S)2-(phosphonooxy)-1-oxo-3-phenylpropyl]amino]benzoic acid (phenylmethyl) ester, calcium salt thereof;
4-[[(S)2-(phosphonooxy)-1-oxo-3-phenylpropyl]amino]benzoic acid, calcium salt thereof;
4-[[(S)2-[[bis(phenylmethoxy)phosphinyl]oxy]-1-oxo-3-phenylpropyl]amino]benzoic acid ethyl ester;
4-[[(S)2-[[hydroxy(phenylmethyl)phosphinyl]oxy]-1-oxo-3-phenylpropyl]amino]benzoic acid ethyl ester, calcium thereof;
4-[[(S)2-[[bis(phenylmethoxy)phosphinyl]oxy]-1-oxo-3-phenylpropyl]amino]benzoic acid (phenylmethyl) ester;
4-[[(S)2-[[hydroxy(2-phenylmethoxy)phosphinyl]oxy]-1-oxo-3-phenylpropyl]benzoic acid phenylmethyl ester, calcium salt thereof;
4-[[(S)2-[[hydroxy(phenylmethoxy)phosphinyl]oxy]-1-oxo-3-phenylpropyl aminobenzoic acid, calcium salt thereof;
4-[[(S)2-[[hydroxy(phenylmethoxy)phosphinyl]oxy]-1-oxo-3-phenylpropyl]amino]benzoic acid ethyl ester;
4-[[(S)2-[[hydroxy(2-phenylethoxy)phosphinyl]oxy]-1-oxo-3-phenylpropyl]amino]benzoic acid ethyl ester, calcium salt thereof;
4-[[(S)2-[[methoxy(2-phenylethoxy)phosphinyl]oxy]-1-oxo-3-phenylpropyl]amino]benzoic acid phenylmethyl ester;
4-[[(S)2-[[hydroxy(2-phenylethoxy)phosphinyl]oxy]-1-oxo-3-phenylpropyl]amino]benzoic acid (phenylmethyl) ester, calcium salt thereof; and
4-[[(S)2-[[hydroxy(2-phenylethoxy)phosphinyl]oxy]-1-oxo-3-phenylpropyl]amino]benzoic acid, calcium salt thereof.

6. A compound defined in claim 1 wherein $R^1$ is hydrogen or $-CHR^{11}OC(O)R^{12}$ {wherein $R^{11}$ and $R^{12}$ are defined in claim 1};

$R^2$ is hydrogen, methoxy, ethoxy or propoxy;

W is hydroxy, alkyl having from 1 to 6 carbon atoms or

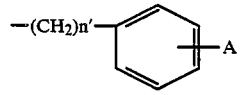

{wherein n' is an integer of from 1-6 and A is hydrogen, fluorine or chlorine};

$VC^*HR^3$ contains an asymmetric carbon ($C^*$) the chirality of which is the S absolute configuration wherein V is oxygen and wherein $R^3$ is

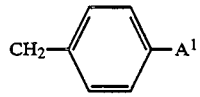

{wherein $A^1$ is hydrogen, fluorine, chlorine or trifluoromethyl}; and

Z is p-phenylene.

7. A compound defined in claim 1 wherein $VC^*HR^3$ contains an asymmetric carbon ($C^*$) the chirality of which is the absolute configuration wherein V is oxygen and wherein $R^3$ is

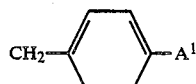

{wherein $A^1$ is hydrogen, fluorine, chlorine or trifluoromethyl}.

8. A compound having the structural formula I:

$$W-P(O)OR^1-V-CHR^3-C(O)-NH-Z-C(O)R^2$$

or a pharmaceutical acceptable salt thereof, wherein:

R¹ is hydrogen, methyl, ethyl, phenyl, benzyl, phenylethyl or —CR¹¹HOC(O)R¹² wherein R¹¹ and R¹² are each independently alkyl having from 1 to 6 carbon atoms or cycloalkyl having from 5 to 7 carbon atoms;

R² is hydroxy, methoxy, ethoxy, propoxy, phenylmethoxy, phenoxyethyloxy, pivaloyloxymethyloxy, —OCH₂CHOHCH₂OH or $$-OCH_2CH-CH_2$$
$$\quad\quad\quad | \quad\quad |$$
$$\quad\quad\quad O \quad\quad O$$
$$\quad\quad\quad\quad \diagdown \diagup$$
$$\quad\quad\quad CH_3 \quad CH_3;$$

W is hydroxy, alkoxy having 1 to 6 carbon atoms, phenylmethoxy, alkyl having from 1 to 6 carbon atoms or $$-(CH_2)_{n'}-\phantom{x}\bigcirc\phantom{x}-A$$

{wherein n' is an integer of from 0–6, and A is hydrogen, fluorine or chlorine};

VC*HR³ contains an asymmetric carbon (C*) the chirality of which is the S absolute configuration wherein V is oxygen or sulfur and wherein R³ is $$-CH_2-\phantom{x}\bigcirc\phantom{x}-A^1$$

wherein A¹ is hydrogen, fluorine, chlorine or trifluoromethyl; and

Z is —CH₂CHR⁴— wherein R⁴ is hydrogen, hydroxy, methoxy, methyl or benzyl.

9. A compound defined in claim 8 having the name:

N-[(S)2(ethoxyethylphosphinyl)oxy]-1-oxo-3-phenylpropyl]β-alanine ethyl ester;

N-[(S)2-[(ethylhydroxyphospninyl)oxy]-1-oxo-3-phenylpropyl]β-alanine ethyl ester, calcium salt thereof;

N-[(S)2-[(ethoxyethylphosphinyl)oxy]-1-oxo-3-phenylpropyl]β-alanine (phenylmethyl) ester;

N-[(S)2-[(ethylhydroxyphosphinyl)oxy]-1-oxo-3-phenylpropyl]β-alanine (phenylmethyl) ester, calcium salt thereof;

N-[(S)2-[(ethylhydroxyphosphinyl)oxy]-1-oxo-3-phenylpropyl]β-alanine, calcium salt thereof;

N-[(S)2-[(ethoxyphenylphosphinyl)oxy]-1-oxo-3-phenylpropyl]β-alanine ethyl ester;

N-[(S)2-(hydroxyphenylphosphinyl)oxy]-1-oxo-3-phenylpropyl]β-alanine ethyl ester, calcium salt thereof;

N-[(S)2-[(ethoxyphenylphosphinyl)oxy]-1-oxo-3-phenylpropyl]β-alanine (phenylmethyl) ester;

N-[(S)2-[(hydroxyphenylphosphinyl)oxy]-1-oxo-3-phenylpropyl]β-alanine (phenylmethyl) ester, calcium salt thereof;

N-[(S)2-[(hydroxyphenylphosphinyl)oxy]-1-oxo-3-phenylpropyl]β-alanine, calcium salt thereof;

N-[(S)2-[(ethoxy(phenylmethyl)phosphinyl]oxy]-1-oxo-3-phenylpropyl]β-alanine ethyl ester;

N-[(S)2-[[hydroxy(phenylmethyl)phosphinyl]oxy]-1-oxo-3-phenylpropyl]β-alanine ethyl ester, calcium salt thereof;

N-[(S)2-[[ethoxy(phenylmethyl)phosphinyl]oxy]-1-oxo-3-phenylpropyl]β-alanine (phenylmethyl) ester;

N-[(S)2-[[hydroxy(phenylmethyl)phosphinyl]oxy]-1-oxo-3-phenylpropyl]β-alanine (phenylmethyl) ester, calcium salt thereof;

N-[(S)2-[[hydroxy(phenylmethyl)phosphinyl]oxy]-1-oxo-3-phenylpropyl]β-alanine;

N-[(S)2-[[ethoxy(2-phenylethyl)phosphinyl]oxy]-1-oxo-3-phenylpropyl]β-alanine ethyl ester;

N-[(S)2-[[hydroxy(phenylethyl)phosphinyl]oxy]-1-oxo-3-phenylpropyl]β-alanine ethyl ester, calcium salt thereof;

N-[(S)2-[[ethoxy(2-phenylethyl)phosphinyl]oxy]-1-oxo-3-phenylpropyl]β-alanine (phenylmethyl) ester;

N-[(S)2-[[hydroxy(2-phenylmethyl)phosphinyl]oxy]-1-oxo-3-phenylpropyl]β-alanine (phenylmethyl) ester, calcium salt thereof;

N-[(S)2-[[hydroxy(2-phenylethyl)phosphinyl]-1-oxo-3-phenylpropyl]β-alanine, calcium salt thereof;

N-[(S)2-[[ethoxy(3-phenylpropyl)phosphinyl]oxy]-1-oxo-3-phenylpropyl]β-alanine ethyl ester;

N-[(S)2-[[hydroxy(3-phenylpropyl)phosphinyl]oxy]-1-oxo-3-phenylpropyl]β-alanine ethyl ester, calcium salt thereof;

N-[(S)2-[[ethoxy(3-phenylpropyl)phosphinyl]oxy]-1-oxo-3-phenylpropyl]β-alanine (phenylmethyl) ester;

N-[(S)2-[[hydroxy(3-phenylpropyl)phosphinyl]oxy]-1-oxo-3-phenylpropyl]β-alanine (phenylmethyl) ester, calcium salt thereof;

N-[(S)2-[[hydroxy(3-phenylpropyl)phosphinyl]oxy]-1-oxo-3-phenylpropyl]β-alanine, calcium salt thereof;

N-[(S)2-[(dimethoxyphosphinyl)oxy]-1-oxo-3-phenylpropyl]β-alanine ethyl ester;

N-[(S)2-[(phosphonooxy)-1-oxo-3-phenylpropyl]β-alanine ethyl ester, calcium salt thereof;

N-[(S)2-[(dimethoxyphosphinyl)oxy]-1-oxo-3-phenylpropyl]β-alanine (phenylmethyl) ester;

N-[(S)2-[(phosphonooxy)-1-oxo-3-phenylpropyl]β-alanine (phenylmethyl) ester, calcium salt thereof;

N-[(S)2-[(phosphonooxy)-1-oxo-3-phenylpropyl]β-alanine, calcium salt thereof;

N-[(S)2-[[bis(phenylmethoxy)phosphinyl]oxy]-1-oxo-3-phenylpropyl]β-alanine ethyl ester;

N-[(S)2-[[hydroxy(phenylmethoxy)phosphinyl]oxy]-1-oxo-3-phenylpropyl]β-alanine ethyl ester, calcium salt thereof;

N-[(S)2-[[bis(phenylmethoxy)phosphinyl]oxy]-1-oxo-3-phenylpropyl]β-alanine (phenylmethyl) ester;

N-[(S)2-[[hydroxy(phenylmethoxy)phosphinyl]oxy]-1-oxo-3-phenylpropyl]β-alanine (phenylmethyl) ester, calcium salt thereof;

N-[(S)2-[[hydroxy(phenylmethoxy)phosphinyl]oxy]-1-oxo-3-phenylpropyl]β-alanine, calcium salt thereof;

N-[(S)2-[[methoxy(2-phenylethoxy)phosphinyl]oxy]-1-oxo-3-phenylpropyl]β-alanine ethyl ester;

N-[(S)2-[[hydroxy(2-phenylmethoxy)phosphinyl]oxy]-1-oxo-3-phenylpropyl]β-alanine ethyl ester, calcium salt thereof;

N-[(S)2-[[methoxy(2-phenylethoxy)phosphinyl]oxy]-1-oxo-3-phenylpropyl]β-alanine (phenylmethyl) ester;

N-[(S)2-[[hydroxy(2-phenylethoxy)phosphinyl]oxy]-1-oxo-3-phenylpropyl]β-alanine (phenylmethyl) ester, calcium salt thereof; or N-[(S)2-[[hydroxy(2-phenylethoxy)phosphinyl]oxy]-1-oxo-3-phenylpropyl]β-alanine, calcium salt thereof.

* * * * *